United States Patent [19]

Moore

[11] Patent Number: Plant 5,328

[45] Date of Patent: Nov. 13, 1984

[54] ROSE PLANT

[75] Inventor: Ralph S. Moore, Visalia, Calif.

[73] Assignee: Sequoia Nursery, Visalia, Calif.

[21] Appl. No.: 458,144

[22] Filed: Mar. 14, 1983

[51] Int. Cl.[3] ..... A01H 5/00

[52] U.S. Cl. ..... Plt./7

[58] Field of Search ..... Plt./7

*Primary Examiner*—Bagwill Robert E.

[57] ABSTRACT

This invention relates to a new and distinct variety of miniature rose plant primarily identified by its very double variegated (striped) buds and flowers of red and white.

1 Drawing Figure

1

The present invention relates to a new and distinct variety of hardy, dwarf, bush type rose plant of the miniature class; the variety being primarily characterized—as to novelty—by the very double red and white striped flowers which generally open to a cupped or rounded form and hold colors extremely well.

The variety is further characterized by:

An abundance of bloom, with flowers usually borne singly, but also several to the stem in a small cluster. Little or no fragrance.

A plant which is vigorous, of rounded, to spreading shape with small semi-glossy to matt foliage with pointed leaflets; the buds and flowers being similar in form to Easter Morning (miniature—U.S. Plant Pat. No. 2,177, expired).

The plant, which has a normal height of 10–14 inches, can easily be maintained at a lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif., under conditions of careful control and observation, as a cross between Little Darling (U.S. Plant Pat. No. 1,582, expired—floribunda) as the seed parent and an un-named seedling (miniature) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety identification: MORmum (Commercial synonym; STRANGE MUSIC)

Flowers borne: Singly and several together (3 to 5) on sturdy, wirey stems.

Quantity of bloom: Abundant both outside and in greenhouse.

2

Bud:

*Peduncle.*—Medium length; slender but sturdy; erect; medium green, sometimes tinted bronze (outdoors); with numerous prickles varying from short thorns to small hair-like appendages.

*Before calyx breaks.*—Size — small. Form — ovoid to pointed, with numerous small foliaceous appendages and hairs on surface of bud; with foliaceous parts extending beyond the tip of the bud equal to less than one-half of its length. Color — medium green, occasionally tinted with bronze (outdoors).

*As calyx breaks.*—Color — silvery to pinkish white tinted with red on petal tip.

*Opening.*—Opens well in all weather.

Bloom:

*Size when fully open.*—Small, averaging about 35–40 mm (1½").

*Petalage.*—Very double — averaging about 80 (or more) petals, arranged regularly plus several small petaloids.

*Form.*—Cupped at first becoming rounded with petals rolled loosely outward and downward. Open flowers usually have no stamens.

Petals: Fairly thick; satiny on inside and on outside surface.

*Shape.*—Outside petals, broad lanceolate (wedge shaped) with rounded tip and very short acute tip; intermediate — broad lanceolate with nearly round or short acute tip; inside — lanceolate with acute tip.

Color. (newly opened flower from a plant grown in plastic greenhouse (November 1982), Visalia, Calif.);

*Outside petal.*—Outside surface — white or pinkish white with some red showing through from inside surface — often tinted deeper pink on tip of petal. Inside surface — striped or variegated with red and white in varying patterns, some flowers having more red than white with other flowers predominately white with less red area; the red areas being near Cardinal Red 822 (or lighter). Opening and freshly opened flowers may have the white areas tinted soft yellow. Basal ⅓ of petal is white or near white.

*Intermediate petal.*—Outside surface similar to outside petal. Inside surface similar to outside petal.

*Inner petal.*—Outside surface — similar to intermediate petal; inside surface — similar to intermediate petal. General color effect; newly opened flowers — red and white stripes (or variegation)

with no two petals alike and no two flowers alike. Three days open — color — similar to fresh open flower, but less bright. Behavior — opens well in all weather. Spent petals or flowers drop off. Flower longevity (July-August 1982) — plant in pot 8-10 days or longer. Cut flowers at living room temperature 5-7 days or longer.

Reproductive organs:

*Stamens.*—Usually none.

*Filaments.*—Usually none.

*Anthers.*—Usually none.

*Pollen.*—None.

*Pistils.*—Small number.

*Styles.*—Varying length; near white; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; medium small; leathery; semi-glossy to matt.

*Leaflets.*—Shape: broad, lanceolate; apex acute; base — acute — sometimes rounded.

*Color.*—Medium green; new growth — normal (medium) green (sometimes tinted reddish).

*Rachis.*—Medium strength; upperside may have a few short hairs; grooved; underside may have several small thorns (or claws) and few to several tiny short prickles.

*Stipules.*—Medium to short length; medium width; medium to short length narrow points which turn out usually at about 45 degrees or more.

Growth:

*Habit.*—Dwarf; bushy; rounded; much branched.

*Growth.*—Moderately vigorous; internodes short.

*Canes.*—Medium; slender sturdy.

*Main stems.*—Color: medium green.

*Thorns.*—Numerous, of varying size and length — usually straight. Hairs — few or none.

The minature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers variegated to striped, in differing degrees and patterns, with red and white, the bud being pointed in the early opening stage, resembling in form Easter Morning (miniature — U.S. Plant Pat. No. 2,177, expired), with the open flower being very full (double) and rounded with many (80 or more) petals; and further characterized by a plant of compact, vigorous, well rounded shape, with main stems and shoots quite thorny, the said plant being easy to propagate from soft wood cuttings with an abundance of small semi-glossy to matt foliage, the flowers being borne singly or several together in clusters on medium to short length stems.

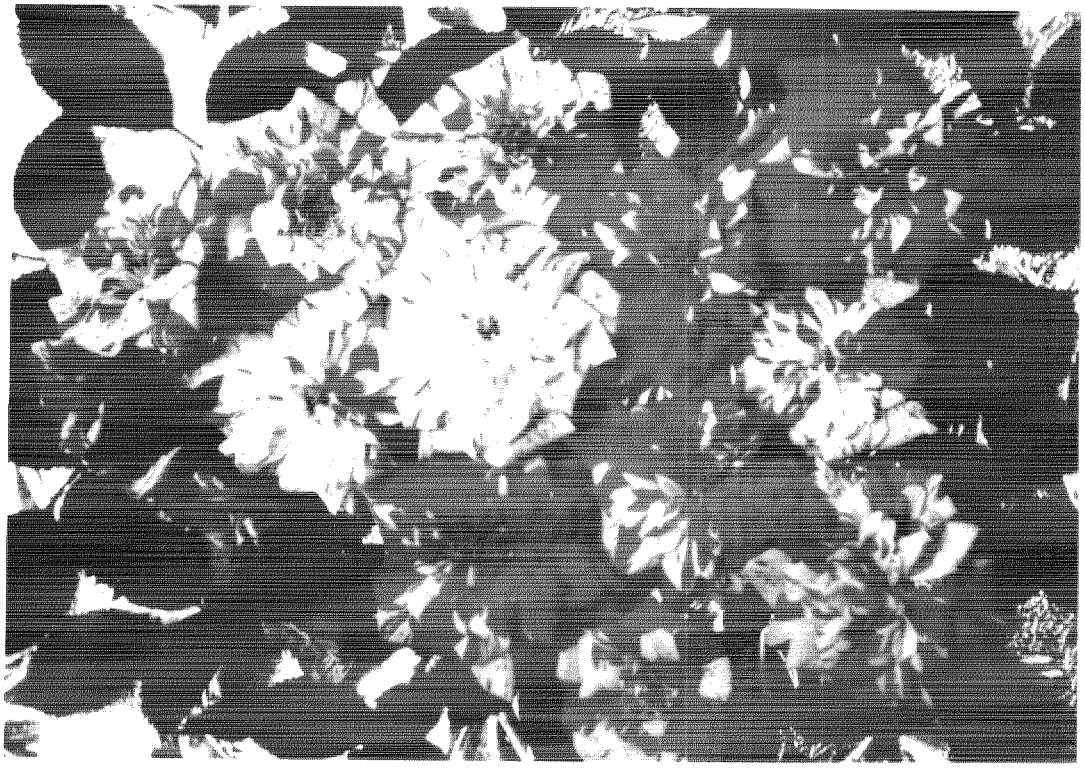

* * * * *